United States Patent [19]

Tadanier et al.

[11] 4,196,197
[45] Apr. 1, 1980

[54] 2'N-ACYL AND ALKYL-6'-N-ALKYL- AND 6',6'-DI-N-ALKYL DERIVATIVES OF FORTIMICINS A AND B

[75] Inventors: John S. Tadanier; Jerry R. Martin, both of Waukegan, Ill.

[73] Assignee: Abbott Laboratories, North Chicago, Ill.

[21] Appl. No.: 863,008

[22] Filed: Dec. 21, 1977
(Under 37 CFR 1.47)

[51] Int. Cl.$^2$ .................. A61K 31/71; C07H 15/22
[52] U.S. Cl. ........................ 424/180; 536/17 R; 536/4
[58] Field of Search .............. 424/180; 536/17, 4

[56] References Cited
U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,060,682 | 11/1977 | Umezawa et al. | 536/17 |

*Primary Examiner*—Johnnie R. Brown
*Attorney, Agent, or Firm*—Robert L. Niblack; Gildo E. Fato; Joyce R. Niblack

[57] ABSTRACT

Novel fortimicin derivatives represented by the formula

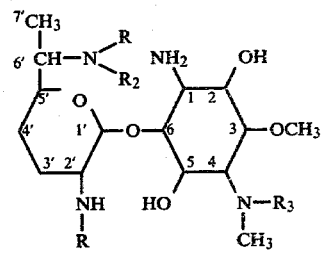

wherein: R is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl or N,N-diloweralkylaminohydroxyloweralkyl; $R_1$ is loweralkyl, $R_2$ is hydrogen or lower alkyl; and $R_3$ is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen and the pharmaceutically acceptable salts thereof; pharmaceutical compositions containing the compounds; and methods of making and using the compounds. The compounds are useful as antibiotics.

10 Claims, No Drawings

2'-N-ACYL AND ALKYL-6'-N-ALKYL- AND 6',6'-DI-N-ALKYL DERIVATIVES OF FORTIMICINS A AND B

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide compounds which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. It is known that in the naturally occurring fortimicin aminoglycoside antibiotics blocking the 2-hydroxy group inactivates the antibiotic.

The present invention provides new and useful fortimicin derivatives.

SUMMARY OF THE DISCLOSURE

2'-N-acyl and alkyl-6'-N-alkyl and 6',6'-di-N-alkyl fortimicin B and derivatives, 4,2'-N,N'-diacyl and dialkyl-6-N-alkyl and 6',6'-di-N-alkyl fortimicin B derivatives, 4-N-acyl-2'-N-alkyl 6'-N-alkyl and 6',6'-di-N-alkyl and 4-N-alkyl-2'-N-acyl-6'-N-alkyl and 6',6'-di-N-alkyl fortimicin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 1 to about 100 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other fortimicin B derivatives which have anti-bacterial activity.

The base fortimicin derivatives of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 2'-N-acyl and alkyl fortimicin B and derivatives, 4,2'-N,N'-diacyl and dialkyl derivatives, 4-N-alkyl-2-N acyl and 4-N-acyl-2'-N-alkyl fortimicin B derivatives represented by Formula I:

wherein R is acyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, aminohydroxyloweralkyl, N-loweralkylaminoloweralkyl, N,N-diloweralkylaminoloweralkyl, hydroxyloweralkyl, N-loweralkylaminohydroxyloweralkyl or N,N-diloweralkylaminohydroxyloweralkyl; $R_1$ is loweralkyl; $R_2$ is hydrogen or lower alkyl; and $R_3$ is acyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, and the pharmaceutically acceptable salts thereof.

The term "pharmaceutically acceptable salts" refers to non-toxic acid addition salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula $$-\overset{O}{\underset{\|}{C}}-R_1$$

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

All amino acid residues are in the natural or L-configuration unless otherwise specified and include, but are not limited to glycyl, alanyl, sarcosyl, tyrosyl, phenylalanyl, methionyl, seryl, lysyl, asparaginyl, isoleucyl, leucyl, histidyl, threonyl, aspartyl, asparaginyl, valyl, prolyl, glutaminyl, tryptophanyl, glutamyl and the like.

The 2'-N-acylfortimicin B derivatives of Formula I can be prepared by rearrangement of the corresponding 4-N-substituted fortimicins B of Formula II

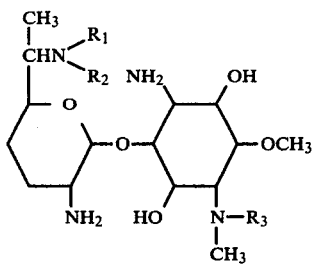

wherein R₁, R₂ and R₃ are as defined in Formula I.

Fortimicin A and fortimicin B are prepared according to the method of U.S. Pat. Nos. 3,976,768 and 3,931,400, respectively. The preparation of representative 4-N-acyl fortimicin B derivatives is set forth in the examples herein.

Generally speaking the compounds of this invention can be prepared by initially converting fortimicin B to 1,2'-di-N-benzyloxycarbonylfortimicin B by, for example, treatment with a suitable acylating agent such as N-(benzyloxycarbobenzyloxy)succinimide. 1,2'-Di-N-benzyloxycarbonyl fortimicin B is then treated with an aromatic aldehyde such as benzaldehyde, followed by treatment with a suitable metal hydride reducing agent such as sodium borohydride, zinc borohydride, or lithium borohydride, resulting in a 6'-arylmethyl derivative. For example, when the aromatic aldehyde chosen is benzaldehyde, the resulting intermediate is 1,2'-di-N-benzyloxycarbonyl-6'-N-benzylfortimicin B. The 6'-N-benzyl derivative can then be subjected to reductive alkylation with an aliphatic aldehyde such as formaldehyde, acetaldehyde, propionaldehyde, butyraldehyde, etc., and the resulting product is subjected to hydrolysis in the presence of an aldehyde scavenger such as hydroxylamine hydrochloride or methoxylamine hydrochloride to obtain the desired 1,2'-di-N-benzyloxycarbonyl-6'-N-benzyl-6'-N-loweralkylfortimicin B in which the 6'-N-loweralkyl group is derived from the aliphatic aldehyde chosen. For example, reductive alkylation with formaldehyde results in the 6'-N-loweralkyl group being methyl, and the resulting product is 1,2'-di-N-benzyloxycarbonyl-6'-N-benzyl-6'-N-methylfortimicin B. With acetaldehyde the 6'-N-loweralkyl group is ethyl, and the product is 1,2'-di-N-benzyloxycarbonyl-6'-N-benzyl-6'-N-ethylfortimicin B, etc.

The C₄-N-methylamino group of 1,2'-di-N-benzyloxycarbonyl-6'-N-benzyl-6'-N-alkylfortimicin B can be conveniently acylated with, for example, an activated carboxylic acid derivative such as a carboxylic acid anhydride, a carboxylic acid derivative such as a carboxylic acid ester or a carboxylic acid azide, following the methodology commonly used in peptide synthesis to obtain the corresponding 4-N-acyl intermediates. The above referred to active carboxylic acid esters can be prepared by reacting the appropriate carboxylic acid,

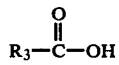

with, for example, 1-hydroxy benzotriazole-N-hydroxysuccinimide, N-hydroxy-5-norbornene-2,3-dicarboximide according to the method of Fugino et al., *Chem. Pharm. Bull Japan,* 22, 1857 (1974). For example, when the acylating agent N-hydroxysuccinimide ester of N-benzyloxycarbonyglycine is reacted with 1,2'-di-N-benzyloxycarbonyl-6'-N-benzyl-6'-N-methylfortimicin B, the resulting product is tri-N-benzyloxycarbonyl-6'-N-benzyl-6'-N-methylfortimicin A. If, for example, the acylating agents are the N-hydroxy-succinimide esters of N-benzyloxycarbonylsarcosine and N-benzyloxycarbonyl-beta-alanine, and they are reacted with tri-N-benzyloxycarbonyl-6'-N-benzyl-6'-N-methylfortimicin B, tri-N-benzyloxycarbonyl-4-N-sarcosyl-6'-N-benzyl-6'-N-methylfortimicin B and tri-N-benzyloxycarbonyl-4-N-beta-alanyl-6'N-benzyl-6'-N-methylfortimicin B are respectively obtained.

Alternately, 1,2'-di-N-benzyloxycarbonylfortimicin B can be subjected to reductive alkylation in the presence of a lower aliphatic aldehyde such as formaldehyde, and the resulting product subjected to hydrolysis in the presence of an aldehyde scavenger such as hydroxylamine hydrochloride or methoxylamine hydrochloride, to obtain a 1,2'-di-N-benzyloxycarbonyl-6',6'-di-N-loweralkylfortimicin B in which the 6'-loweralkyl groups are derived from the aldehyde chosen. For example, when the lower aliphatic aldehyde is formaldehyde, the product is 1,2'-di-N-benzyloxycarbonyl-6',6'-di-N-methylfortimicin B. When the aliphatic aldehyde is acetaldehyde the product is 1,2'-di-N-benzyloxycarbonyl-6',6'-di-N-ethylfortimicin B. When the aliphatic aldehyde is propionaldehyde, the product is 1,2'-di-N-benzyloxycarbonyl-6',6'-di-N-di-n-propylfortimicin B, etc.

The 1,2'-di-N-benzyloxycarbonyl-6',6'-di-N-alkylfortimicins B intermediate can be condensed with suitable acylating agents, as described above, to obtain the corresponding 4-N-acyl derivatives. For example, when the acylating agent is the N-hydroxysuccinimide ester of N-benzyloxycarbonylglycine, and is reacted with 1,2'-di-N-benzyloxycarbonyl-6',6'-di-N-methylfortimicin B, the resulting product is tri-N-benzyloxycarbonyl-6',6'-di-N-dimethylfortimicin A. If the acylating agents are the N-hydroxysuccinimide esters of N-benzyloxycarbonylsarcosine and N-benzyloxycarbonyl-beta-alanine, and are, for example, reacted with 1,2'-di-N-benzyloxycarbonyl-6',6'-di-N-methylfortimicin B, the products are tri-N-benzyloxycarbonyl-6',6'-di-N-methyl-4-N-sarcosylfortimicin B and tri-N-benzyloxycarbonyl-6',6'-di-N-dimethyl-4-N-beta-alanylfortimicin B, respectively.

Removal of the benzyloxycarbonyl or other aryloxycarbonyl protecting groups, as well as the benzyl or other aryl protecting groups is accomplished by hydrogenolysis, using a suitable catalyst, such as palladium on carbon. For example, when the 1,2'-di-N-benzyloxycarbonyl-6'-N-alkyl-6'-N-benzylfortimicins of this invention are subjected to catalytic hydrogenolysis, in the presence of, for example, 5% palladium on carbon, the desired compounds of Formula I are formed by replacement of the 6'-N-benzyl group and the benzyloxycarbonyl groups by hydrogen atoms to give 6'-N-alkylfortimicins which can be conveniently isolated as their acid chloride salts. For example, hydrogenolysis of 1,2'-di-N-benzyloxycarbonyl-6'-N-benzyl-6'-N-methylfortimicin B gives 6'-N-methylfortimicin B which can conveniently be isolated as the perhydrochloride salt. Similar hydrogenolysis of, for example, tri-N-benzyloxycarbonyl-6'-N-benzyl-6'-N-methylfortimicin A, tri-N-benzyloxycarbonyl-4-N-sarcosyl-6'-N-benzyl-6'-N-methylfortimicin B and tri-N-benzyloxycarbonyl-4-N-beta-alanyl-6'-N-benzyl-6'-N-methylfortimicin B yields 6'-N-methyl-6'-N-methylfortimicin A, 4-N-sarcosyl-6'-N- methylfortimicin B, and 4-N-beta-alanyl-6'-N-methyl-fortimicin B, respectively.

Similarly, when the 1,2'-di-N-benzyloxycarbonyl-6',6'-di-N-loweralkylfortimicins are subjected to catalytic hydrogenolysis in the presence of a suitable catalyst, the benzyloxycarbonyl groups are replaced by hydrogen to give the desired 6',6'-di-N-loweralkylfortimicin. For example, catalytic hydrogenolysis of tri-N-benzyloxycarbonyl-6',6'-di-N-methylfortimicin B in the presence of 5% palladium on carbon in 0.2 N hydrochloric acid in methanol gives 6',6'-di-N-methylfortimicin B as the perhydrochloride salt. Similar hydrogenolysis of tri-N-benzyloxycarbonyl-6',6'-di-N-methylfortimicin A, tri-N-benzyloxycarbonyl-4-N-sarcosyl-6',6'-di-N-methylfortimicin B and tri-N-benzyloxycarbonyl-4-N-beta-alanyl-6',6'-di-N-methylfortimicin B results in the compounds 6',6'-di-N-dimethylfortimicin A, 4-N-sarcosyl-6',6'-di-N-methylfortimicin B, and 4-N-beta-alanyl-6',6'-di-N-methylfortimicin B, respectively, which can be isolated as, for example, their tetrahydrochloride salts.

The 2'-N-acyl derivatives of this invention can then be conveniently prepared by initially converting the corresponding 4-N-acyl, 2'-N-alkyl or 2',2'-di-N-alkyl fortimicins to the free bases by, for example, by use of a suitable anion exchange resin. The 2'-N-substituted fortimicins B are then prepared by placing the 4-N-substituted fortimicin free bases in water solution which readily rearranges the $C_4$ carbon substituent to the $C_2$, carbon atom. Treatment of the 2'-N-substituted fortimicins B with suitable N-acetylating agents such as N-(benzyloxycarbonyloxy)succinimide, benzyloxycarbonyl chloride or O-(benzyloxycarbonyl)p-nitrophenol in a solvent system such as N,N-dimethylformamide-methanol-water results in the 1,2',6'-tri-N protected intermediate, i.e., 1,2'-6'-N,N',N''-tribenzyloxy intermediate, which can be acetylated with a variety of activated carboxylic acid derivatives, such as a carboxylic acid anhydride, a carboxylic acid chloride, an active carboxylic acid ester, or a carboxylic acid azide.

The active esters may be conveniently prepared by reacting the appropriate carboxylic acid,

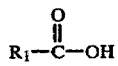

with, for example, 1-hydroxybenzotriazole, N-hydroxysuccinimide, or N-hydroxy-5-norborene-2,3-dicarboximide according to the method of M. Fujino et al., *Chem. Pharm. Bull, Japan*, 22, 1857 (1974) wherein $R_1$ is an acyl group as defined in Formula I.

After completion of the N-acylation of the $C_4$-N-methylamino group, it is necessary to remove the benzyloxycarboxyl protecting groups, which can conveniently be carried out by hydrogenolysis over a palladium on carbon catalyst. The fortimicin analogs thus prepared are conveniently isolated as the hydrochloride salts (or other acid addition salts) when the hydrogenolysis is carried out in the presence of a slight excess of hydrochloric acid or another suitable acid.

The 2',6'-di-N-alkyl or 6',6'-N,N-dialkyl alkylfortimicins of this invention are conveniently prepared by treatment of the 2'-N-acylfortimicins B with a suitable reducing agent such as a hydride or diborane or a metal hydride such as lithium aluminum hydride. The resulting 2'-N-alkylfortimicins B derivative can then be treated with a suitable N-acylating agent as described above leaving the $C_4$-methylamino group free. $C_4$-N-acylation and deblocking as described previously gives the 4-N-acyl-2'-N-alkylfortimicins B.

The 4,2'-di-N-alkylfortimicins B are conveniently prepared by treating the desired N-protected 2'-N-acylfortimicin B with a suitable reducing agent, e.g., the hydride of diborane. Deblocking by hydrogenolysis as described above gives 4,2'-di-N-alkylfortimicins B. Alternatively, the 4,2'-di-N-alkylfortimicins can be prepared by reducing of a suitable 4'-N-acyl-2'-N-alkylfortimicin B. For example, a 4-N-acyl-2'-N-alkylfortimicin B or an N-protected 4-N-acyl-2'-N-alkylfortimicin B may be treated with a suitable reducing agent, e.g., diborane. In the case of the resulting N-protected 4,2'-di-N-alkylfortimicins B, the N-blocking groups can be conveniently removed by hydrogenolysis providing the 4,2'-di-N-alkylfortimicin B.

Alternatively, the 2'-N-acyl derivatives of this invention can be prepared by reacting fortimicin B with tert-butyl-S-(4,6-dimethyl-pyrimidin-2-yl) thiolcarbonate to obtain the 2'-tert-butyloxycarbonyl (Boc) fortimicin B intermediate.

The 2'-Boc-Intermediate is then reacted with a suitable acylating agent, i.e., N-(benzyloxycarbonyloxy)-succinimide which results in the 1,6'-di-N-benzyloxy-2'-Boc-fortimicin B intermediate. Treatment of the latter intermediate with benzyloxycarbonylglycine in the presence of a suitable solvent system such as N,N-dimethylformamide-methanol-water results in the 2'-Boc-tribenzyloxycarbonylfortimicin B intermediate.

Deprotection of the 2'-amino group is effected by reacting the latter intermediate with, for example, $CF_3COOH$. 2'-acylation is then conveniently accomplished by reacting the latter 2'-deprotected intermediate with a suitable aldehyde ($R_1CHO$) or carboxylic acid ester as described above, in the presence of sodium borohydride. Deprotection is then completed by hydrogenolysis in the presence of 5% palladium on carbon catalyst which results in the desired 2'-alkyl or 2'-acyl derivatives.

The following examples further illustrate the present invention.

EXAMPLE 1

1,2'-Di-N-benzyloxycarbonylfortimicin B

To a magnetically stirred solution of 10 g. of fortimicin B, 150 ml. of water, 300 ml. of methanol, and 4.95 ml. of glacial acetic acid (solution pH 6), cooled to 0° in an ice bath, is added 15.7 g. of N-(benzyloxycarbonyl)-succinimide. Stirring is continued at 0° for 1.5 hours, and the solution is then allowed to stand at ambient temperature for 25 hours. The resulting solution is concentrated to one-third volume under vacuum and then extracted with chloroform. The chloroform solution is washed with 1% aqeuous sodium bicarbonate and dried over anhydrous magnesium sulfate. The chloroform is evaporated under reduced pressure and residual solvent is removed by co-distillation with benzene under reduced pressure to give 19 g. of product. A sample of 96 g. of product prepared as above is chromatographed on a 7.0 cm O.D. (outside diameter) column packed to a height of 80 cm with a slurry of silica gel and a solvent system composed of chloroform:methanol:concentrated ammonium hydroxide (750:150:7). Elution is carried out with the solvent system yielding 36 g. of pure 1,2'-di-N-benzyloxycarbonylfortimicin B as a white powder: $[\alpha]_D^{22} + 43°$ (c 1%, $CH_3OH$); NMR ($CDCl_3$) $\delta$ 0.81 d ($C_{6'}$—$CH_3$, $J_{6',7'}$=Hz), 2.32 (N—$CH_3$), 3.41; IR (CDCl$_3$) 3562, 3432, 1712 cm$^{-1}$.

Elemental analysis is in agreement with the empirical formula $C_{31}H_{44}N_4O_9$.

An additional 8.9 g. of 1,2'-di-N-benzyloxycarbonyl-fortimicin B of slightly lower purity is obtained from earlier chromatography fractions.

EXAMPLE 2

1,2'-Di-N-benzyloxycarbonyl-6'-N-benzylfortimicin B

A solution prepared from 0.617 g. of 1,2'-di-N-benzyloxycarbonylfortimicin B, 0.25 ml. of benzaldehyde, and 6.0 ml. of methanol is heated under reflux for 0.5 hours. To the resulting magnetically stirred solution, cooled to room temperature is added a freshly prepared solution of 0.1041 g. of sodium borohydride in 0.6 ml. of water. Stirring is continued at room temperature for 4 hours. The resulting solution is shaken with a mixture of 100 ml. of chloroform and 200 ml. of water. The chloroform solution is separated and washed with 200 ml. of water. The aqueous solutions are washed in series with three 100 ml. portions of chloroform. The chloroform solutions are combined and dried over anhydrous magnesium sulfate. Evaporation of the chloroform under reduced pressure leaves 0.816 g. of a sticky white glass. The product is chromatographed on 80 g. of silica gel packed to a height of 47 cm in a 2.4 cm O.D. column in a slurry with 160 ml. of a solvent system prepared from chloroform:methanol:concentrated ammonium hydroxide (19:1:0.2). Elution is carried out with the solvent system to yield 0.414 g. of 1,2'-di-N-benzyloxycarbonyl-6'-N-benzylfortimicin B: $[\alpha]_D^{23}$+43° (c 1%, CH$_3$OH); NMR: (CDCl$_3$) δ 0.90 d ($C_{6'}$—$CH_3$, $J_{6',7'}$=7 Hz); 2.37 (N—$CH_3$); 3.39 (OCH$_3$); IR: (CDCl$_3$) 3552, 3434, 3420, 1698 cm$^{-1}$.

Elemental analysis is in agreement with the empirical formula $C_{38}H_{50}N_4O_9$.

EXAMPLE 3

1,2'-Di-N-benzyloxycarbonyl-6'-N-benzyl-6'-N-methyl-fortimicin B

A solution of 3 g. of 1,2'-di-N-benzyloxycarbonyl-6'-N-benzylfortimicin B in 220 ml. of methanol, in the presence of 10 ml. of 37% formalin and 3 g. of 5% platinum on carbon, is catalytically hydrogenated under three atmospheres of hydrogen for 6.5 hours. The catalyst is removed by filtration, and the solvent is removed under high vacuum leaving 2.71 g. of sticky, white glass. A sample of 2.4 g. of the product is chromatographed on 160 g. of silica gel packed to a height of 50 cm in a 3.4 cm O.C. column in a slurry with 320 ml. of a solvent system of methylene chloride: methanol:37% formalin. Elution is carried out with the solvent system to give 1.79 g. of the methylene 4,5-oxazolidine derivative of 1,2'-di-N-benzyloxycarbonyl-6'-N-benzyl-6'-N-methylfortimicin B: NMR (CDCl$_3$) δ 0.86 d ($C_{6'}$—$CH_3$, $J_{6',7'}$=6.8 Hz); 2.18, 2.30 (N—$CH_3$); 3.47 (OCH$_3$); 3.83d, 4.63d (—OCH$_2$NCH$_3$'$J_{AB}$=2.5 Hz).

A solution of 1.74 g. of the above prepared 4,5-oxazolidine derivative, 0.57 g. of hydroxylamine hydrochloride, 1.5 ml. of glacial acetic acid, and 100 ml. of methanol is heated under reflux for 0.5 hours. The major portion of the methanol is removed under reduced pressure and the residue is shaken with a mixture of dilute ammonium hydroxide and chloroform. The chloroform solution is separated and washed with saturated aqueous sodium chloride. The aqueous solutions are washed in series with three portions of chloroform. The chloroform solutions are combined and dried over anhydrous magnesium sulfate. Evaporation of the chloroform under vacuum yields 1.69 g. of 1,2'-di-N-benzyloxycarbonyl-6'-N-benzyl-6'-N-methylfortimicin B.

$[\alpha]_D^{24}$+39° (c 1%, CH$_3$OH); NMR: (CDCl$_3$) δ 0.93 d ($C_{6'}$—$CH_3$, $J_{6',7'}$=7 Hz); 2.15, 2.31 (N—$CH_3$), 3.42 (OCH$_3$); IR (CDCl$_3$) 3550, 3420, 1700 cm$^{-1}$.

Elemental analysis is in agreement with the empirical formula $C_{39}H_{52}N_4O_9$.

EXAMPLE 4

Tri-N-benzyloxycarbonyl-6'-N-benzyl-6'-N-methylfortimicin A

To a magnetically stirred solution of 0.706 g. of 1,2'-di-N-benzyloxycarbonyl-6'-N-benzyl-6'-N-methylfortimicin B in 9 ml. of tetrahydrofuran, cooled to 0° in an ice bath, is added 0.416 g. of the N-hydroxysuccinimide ester of N-benzyloxycarbonylglycine. Stirring is continued at 0° for 3 hours and then at ambient temperature for 20 hours. The resulting solution is shaken with a mixture of 200 ml. of 5% aqueous sodium bicarbonate and 200 ml. of chloroform. The chloroform solution is separated and washed with 200 ml. of water. The aqueous solutions are washed in series with three 100-ml. portions of chloroform. The chloroform solutions are combined and the chloroform is evaporated under reduced pressure leaving 1.00 g. of white glass. A sample of 0.97 g. of the product is chromatographed on 80 g. of silica gel packed to a height of 49 cm in a 2.4 cm O.D. column in a slurry with 160 ml of a solvent system of ethyl acetate: triethylamine (19.8:0.2). Elution was carried out with the solvent system to yield 0.768 g. of tri-N-benzyloxycarbonyl-6'-N-benzyl-6'-N-methyl-fortimicin A: $[\alpha]_D^{22}$+53° (c 1%, CH$_3$OH); NMR: (CDCl$_3$) δ 1.01 d ($C_{6'}$—$CH_3$, $J_{6',7'}$=6.5 Hz); 2.17 (NCH$_3$CH$_2$Ph), 2.78 (NCH$_3$COCH$_2$NHZ), 3.28 (OCH$_3$); IR (CDCl$_3$) 3550, 3410, 1702, 1627 cm$^{-1}$.

Elemental analysis is in agreement with the empirical formula $C_{49}H_{61}N_5O_{12}$.

EXAMPLE 5

1,2'-Di-N-benzyloxycarbonyl-6',6'-di-N-methylfortimicin B

A solution prepared from 3.02 g. of 1,2-di-N-benzyloxycarbonylfortimicin B, 5 ml of 37% formalin, and 195 ml. of methanol is hydrogenated under 3 atmospheres of hydrogen for 4.5 hours in the presence of 1.5 g. of 5% platinum on carbon. The catalyst is removed by filtration and the solvent is evaporated under reduced pressure leaving 3.04 g. of product. The latter, in a solution with 5 ml. of formalin and 195 ml. of methanol, is hydrogenated under 3 atmospheres of 5% platinum on carbon. The catalyst is removed by filtration and the solvent is evaporated under reduced pressure, leaving 2.43 g. of the 4,5-methylene oxazolidine derivative of 1,2'-di-N-benzyloxycarbonyl-6',6'-di-N-methylfortimicin B: NMR (CDCl$_3$) δ 0.83d ($C_{6'}$—$CH_3$, $J_{6',7'}$=8 Hz); 2.21, 3.32 (N—$CH_3$), 3.48 (OCH$_3$); Doublet between 3.79–3.86, 4.50d (OCH$_2$NCH$_3$, $J_{AB}$=3 Hz).

A solution prepared from 2.37 g. of the above 4,5-methylene oxazolidine intermediate, 0.840 g. of hydroxylamine hydrochloride, 2.3 ml. of acetic acid and 150 ml. of methanol is heated under reflux for 0.5 hours. The major portion of the methanol is evaporated under reduced pressure and the residue is shaken with a mixture of 300 ml. of dilute ammonium hydroxide solution saturated with sodium chloride, and 200 ml. of chloroform. The chloroform solution is separated and washed with 300 ml. of saturated aqueous sodium chloride solution. The aqueous solutions are washed in series with three 100-ml. portions of chloroform. The chloroform solutions are combined and dried over anhydrous magnesium sulfate. Evaporation of the chloroform leaves 2.30 g. of white glass. The product is chromatographed on 200 g. of silica gel using a solvent system composed of methylene chloride:methanol:concentrated ammonium hydroxide (14:6:0.2) to yield 1.90 g. of 1,2'-di-N-benzyloxycarbonyl-6',6'-di-N-methylfortimicin B: $[\alpha]_D^{22}+44°$ (c 1%, CH$_3$OH); NMR: (CDCl$_3$) δ 0.84d (C$_6$'—CH$_3$, J$_{6',7'}$=7 Hz) 2.18 [N(CH$_3$)$_2$], 2.37 (N—CH$_3$), 3.43 (OCH$_3$); IR (CDCl$_3$) 3557, 3423, 3348, 1695.

Elemental analysis is in agreement with the empirical formula C$_{33}$H$_{48}$N$_4$O$_9$.

EXAMPLE 6

Tri-N-benzyloxycarbonyl-6',6'-di-N-methylfortimicin A

To a magnetically stirred solution of 0.626 g. of 1,2'-di-N-benzyloxycarbonyl-6',6'-di-N-methylfortimicin B in 9 ml. of tetrahydrofuran, cooled in an ice bath, is added 0.4016 g. of the N-hydroxysuccinimide ester of N-benzyloxycarbonylglycine. Stirring is continued at 0° for 3 hours and then at ambient temperature for 22 hours. The resulting solution is shaken with a mixture of 200 ml. of chloroform and 200 ml. of 5% aqueous sodium bicarbonate. The chloroform solution is separated and washed with 200 ml. of water. The aqueous solutions are washed in series with three 100-ml. portions of chloroform. The chloroform solutions are combined and the chloroform is evaporated under reduced pressure leaving 0.8619 g. of white glass. The product is chromatographed on 75 g. of silica gel packed to a height of 46 cm in a 2.4 cm O.D. column in a slurry with 150 ml. of a solvent system of ethyl acetate:methanol:triethylamine (22:2:0.3). Elution is carried out with the solvent system to yield 0.7356 g. of tri-N-benzyloxycarbonyl-6',6'-di-N-methylfortimicin A as a white glass: $[\alpha]_D^{22}+67°$ (c 1%, CH$_3$OH); NMR (CDCl$_3$) δ 0.9d (C$_6$'—CH$_3$, J$_{6',7'}$=6.7 Hz), 2.22 [N(CH$_3$)$_2$], 3.35 (N—CH$_3$—COCH$_2$NHZ), 3.31 (OCH$_3$); IR (CDCl$_3$) 3552, 3412, 1700, 1628 cm$^{-1}$.

Elemental analysis is in agreement with the empirical formula C$_{43}$H$_{57}$N$_5$O$_{12}$.

EXAMPLE 7

Tri-N-benzyloxycarbonyl-4-N-sarcosyl-6'-N-benzyl-6'-N-methylfortimicin B

To a magnetically stirred solution of 0.820 g. of 1,2'-di-N-benzyloxycarbonyl-6'-N-benzyl-6'-N-methylfortimicin B in 10 ml. of tetrahydrofuran, cooled in an ice bath, is added 0.480 g. of the N-hydroxysuccinimide ester of N-benzyloxycarbonylsarcosine. Stirring is continued at 0° for 3 hours and then at ambient temperature for 24 hours. The product is isolated by chloroform extraction and purified by chromatography on silica gel using an ethyl acetate-triethylamine system to give tri-N-benzyloxycarbonyl-4-N-sarcosyl-6'-N-benzyl-6'-N-methylfortimicin B. IR, NMR and elemental analysis are compatible with the structure.

EXAMPLE 8

Tri-N-benzyloxycarbonyl-4-N-beta-alanyl-6'-N-benzyl-6'-N-methylfortimicin B

To a magnetically stirred solution of 0.960 g. of 1,2'-di-N-benzyloxycarbonyl-6'-N-benzyl-6'-N-methylfortimicin B in 12 ml. of tetrahydrofuran, cooled in an ice bath, is added 0.594 g. of the N-hydroxysuccinimide ester of N-benzyloxycarbonyl-beta-alanine. Stirring is continued at 0° for 3 hours and then at ambient temperature for 27 hours. The product is isolated by chloroform extraction and purified by chromatography on silica gel using an ethyl acetate-triethylamine system to give tri-N-benzyloxycarbonyl-4-N-beta-alanyl-6'-N-benzyl-6'-N-methylfortimicin B. IR, NMR and elemental analysis are compatible with the structure.

EXAMPLE 9

Tri-N-benzyloxycarbonyl-4-N-sarcosyl-6',6'-di-N-methylfortimicin B

To a magnetically stirred solution of 0.920 g. of 1,2'-di-N-benzyloxycarbonyl-6',6'-di-N-methylfortimicin B in 12 ml. of tetrahydrofuran, cooled in an ice bath, is added 0.640 g. of the N-hydroxysuccinimide ester of N-benzyloxycarbonylsarcosine. Stirring is continued at 0° for 3 hours and then at ambient temperature for 22 hours. The product is isolated by chloroform extraction and purified by chromatography on silica gel using an ethyl acetate:methanol:triethylamine system to give tri-N-benzyloxycarbonyl-4-N-sarcosyl-6',6'-di-N-methylfortimicin B. IR, NMR and elemental analysis are compatible with the structure.

EXAMPLE 10

Tri-N-benzyloxycarbonyl-4-N-beta-alanyl-6',6'-di-N-methylfortimicin B

To a magnetically stirred solution of 0.885 g. of 1,2'-di-N-benzyloxycarbonyl-6',6'-di-N-methylfortimicin B in 12 ml. of tetrahydrofuran, cooled in an ice bath, is added 0.609 g. of the N-hydroxysuccinimide ester of N-benzyloxycarbonyl-beta-alanine. Stirring is continued at 0° for 3 hours and then at ambient temperature for 24 hours. The product is isolated by chloroform extraction and purified by chromatography on silica gel using a chloroform:methanol:triethylamine system to give tri-N-benzyloxycarbonyl-4-N-beta-alanyl-6',6'-di-N-methylfortimicin B. IR, NMR, and elemental analysis are compatible with the structure.

EXAMPLE 11

6'-N-Methylfortimicin A Tetrahydrochloride

A sample of 0.432 g. of tri-N-benzyloxycarbonyl-6'-N-benzyl-6'-N-methylfortimicin A in the presence of 28.4 ml. of 0.2 N hydrochloric acid in methanol, 6.6 ml. of methanol, 0.430 g. of 5% palladium on carbon is hydrogenated for 4 hours under 3 atmospheres of hydrogen. The catalyst is removed by filtration and the solvent is evaporated under reduced pressure leaving 0.259 g. of 6'-N-methylfortimicin A as the tetrahydrochloride salt in the form of a powder: $[\alpha]_D^{23}+81°$ (c 1%, CH$_3$OH); NMR (D$_2$O) δ 1.81 (C$_6$'—CH$_3$. J$_{6',7'}$=7 Hz); 3.20 (NH$_2$CH$_3$), 3.58 (NCH$_3$COCH$_2$NH$_3$), 3.95 (OCH$_3$); IR (KBr) 1630 cm$^{-1}$.

EXAMPLE 12

6'-N-Methylfortimicin B Tetrahydrochloride

A sample of 0.260 g. of 1,2'-di-N-benzyloxycarbonyl-6'-N-benzyl-6'-N-methylfortimicin B in the presence of 36 ml. of 0.2 N hydrochloric acid in methanol, 14 ml. of methanol and 0.260 g. of 5% palladium on carbon is hydrogenated for 4 hours under 3 atmospheres of hydrogen. The catalyst is removed by filtration and the solvent is evaporated under reduced pressure leaving 0.172 g. of 6'-N-methylfortimicin B as the tetrahydrochloride salt in the form of a powder: $[\alpha]_D^{23} + 81°$ (c 1%, $CH_3OH$); NMR ($D_2O$) δ 1.80 ($C_{6'}$—$CH_3$, $J_{6',7'}$=6.8 Hz), 3.21, 3.28 ($NH_2CH_3$), 3.95 ($OCH_3$).

The mass spectrum is compatible with the empirical formula $C_{16}H_{34}N_4O_5$.

EXAMPLE 13

6',6'-Di-N-methylfortimicin B tetrahydrochloride

A sample of 0.407 g. of 1,2'-di-N-benzyloxycarbonyl-6',6'-di-N-methylfortimicin B in the presence of 50 ml. of 0.2 N hydrochloric acid in methanol and 0.4 g. of 5% palladium on carbon is hydrogenated for 4 hours under 3 atmospheres of hydrogen. The catalyst is removed by filtration and the solvent is evaporated under reduced pressure leaving 0.304 g. of 6',6'-di-N-methylfortimicin B as the tetrahydrochloride salt in the form of a powder: $[\alpha]_D^{24} + 84°$ (c 1%, $CH_3OH$); NMR ($D_2O$) δ 1.76d ($C_{6'}$—$CH_3$, $J_{6',7'}$=6.6 Hz), 3.29, 3.38 [$HN(CH_3)_2$], 3.38 ($NH_2CH_3$), 3.95 ($OCH_3$).

The mass spectrum is compatible with the empirical formula $C_{17}H_{36}N_4O_5$.

EXAMPLE 14

6',6'-Di-N-methylfortimicin A tetrahydrochloride

A sample of 0.350 g. of tri-N-benzyloxycarbonyl-6',6'-di-N-methylfortimicin A in the presence of 33.5 ml. of 0.2 N-hydrochloric acid in methanol, 1.5 ml. of methanol, 0.350 g. of 5% palladium on carbon is hydrogenated for 4 hours under 3 atmospheres of hydrogen. The catalyst is removed by filtration and the solvent is evaporated under reduced pressure leaving 0.2445 g. of 6',6'-di-N-methylfortimicin A as the tetrahydrochloride salt in the form of a white powder: $[\alpha]_D^{23} + 77°$, (c 1%, $CH_3OH$); NMR ($D_2O$) δ 1.76d ($C_{6'}$—$CH_3$, $J_{6',7'}$=6.4 ($OCH_3$); IR (KBr) 1634.

The mass spectrum is in agreement with the empirical formula $C_{19}H_{39}N_5O_6$.

EXAMPLE 15

4-N-beta-Alanyl-6'-N-methylfortimicin B Tetrahydrochloride

Tri-N-benzyloxycarbonyl-4-N-beta-alanyl-6'-N-methylfortimicin B is converted to 4-N-beta-alanyl-6'-N-methylfortimicin B and isolated as the hydrochloride salt according to the process of Example 11.

NMR, IR and the Mass Spectrum are compatible with the Spectrum.

EXAMPLE 16

4-N-Sarcosyl-6'-N-methylfortimicin B Tetrahydrochloride

Tri-N-benzyloxycarbonyl-4-N-sarcosyl-6'-N-benzyl-6'-N-methylfortimicin B is converted to 4-N-sarcosyl-6'-N-methylfortimicin B and isolated as the tetrahydrochloride salt according to the procedure of Example 11.

NMR, IR and the Mass Spectrum are compatible with the structure.

EXAMPLE 17

4-N-beta-Alanyl-6',6'-di-N-methylfortimicin B Tetrahydrochloride

Tri-N-benzyloxycarbonyl-4-N-beta-alanyl-6',6'-di-N-methylfortimicin B is converted to 4-N-beta-alanyl-6',6'-di-N-methylfortimicin B and isolated as the tetrahydrochloride salt according to the process of Example 11.

NMR, IR and the mass spectrum are compatible with the structure.

EXAMPLE 18

4-N-Sarcosyl-6',6'-di-N-methylfortimicin B Tetrahydrochloride

Tri-N-benzyloxycarbonyl-4-N-sarcosyl-6',6'-di-N-methylfortimicin B is converted to 4-N-sarosyl-6',6'-di-N-methylfortimicin B and isolated as the tetrahydrochloride salt according to the process of Example 11.

NMR, IR and the mass spectrum are compatible with the structure.

EXAMPLE 19

2'-N-Glycyl-6'-N-methylfortimicin B

An aqueous solution of 10.0 g. of 6'-N'-methylfortimicin A disulfate (1) is passed through a column of an anion exchange resin, AG ® 2-X8 resin, 100–200 mesh, hydroxyl form, sufficient to remove the sulfate ion. The basic elutes are collected and diluated with water to a 1% solution based on starting fortimicin A disulfate. After standing at 37° C. for 20 days the water is evaporated under reduced pressure to leave an oil. A 2.07 g. portion of the oil is chromatographed on a column (2.2×52 cm) of a cation exchange resin, carboxylic type, e.g., Bio-Rad Laboratories, Bio-Rex 70, (100–200 mesh, ammonium form) and eluted with 0.1 N ammonium hydroxide. Elutes containing only 2'-N-glycyl-6'-N'-methylfortimicin B are collected, evaporated to a small volumn under reduced pressure and lyophilized to give 1.349 g. of product.

EXAMPLE 20

1-N-benzyloxycarbonyl-2'-N-(N-Benzyloxycarbonyl-glycyl)-6'-N-methylfortimicin B A stirred solution of 0.333 g. of 2'-N-glycyl-6'-N-methylfortimicin B in 4.5 ml. of water and 9.0 ml. of methanol cooled to 4° C. in an ice bath, is treated with 0.666 g. of benzyloxycarbonyloxysuccinimide. Stirring is continued at 4° C. for 3 hours and then at room temperature for 20 hours. The resulting solution is concentrated under reduced pressure to an oil. The oil is shaken with a mixture of 150 ml. of chloroform and 75 ml. of water. The chloroform layer is separated and washed with 75 ml. of water. The aqueous portions are washed in series with two 75 ml. portions of chloroform. The chloroform solutions are combined and dried over anhydrous magnesium sulfate. Evaporation of the chloroform under reduced pressure leaves 0.596 g. of product. The product is chromatographed on a column (1.8×48 cm) of silica gel prepared and eluted with a solvent system consisting of chloroform methanol-ammonium hydroxide (23.4:1.4:0.1 v/v) to yield 0.254 g. of the desired product.

EXAMPLE 21

Tri-N-benzyloxycarbonyl-2'-N-glycyl-6'-N-methylfortimicin A

To a stirred solution of 0.234 g. of 1-N-benzyloxycarbonyl-2'-N-(N-benzyloxycarbonylglycyl)-6'-N-methylfortimicin B and 0.939 g of 1-hydroxybenzotriazole monohydrate in 2.0 ml. of tetrahydrofuran is added 0.087 g. of N,N-dicyclohexylcarbodiimide in 2.0 ml. of tetrahydrofuran. Stirring is continued for 20 hours at room temperature. Insoluble dicyclohexylurea is removed by filtration and the filtrate is concentrated to dryness under reduced pressure to give 0.408 g. of lemon-yellow solid. The solid is chromatographed on a column (1.8×42 cm) of silica gel eluted with a solvent system consisting of benzene-methanol-95% ethanol-ammonium hydroxide (23.5:1.4:2.0:0.2 v/v/v/v) to give 0.235 g. of product.

EXAMPLE 22

2'-N-Glycyl-6'-N-methylfortimicin A tetrahydrochloride

A solution of 0.235 g. of tri-N-benzyloxycarbonyl-2'-N-glycyl-6'-N-methylfortimicin A in 40 ml. of 0.2 N hydrochloric acid in methanol is hydrogenolyzed for 4 hours under 3 atmospheres of hydrogen in the presence of 0.235 g. of 5% palladium on carbon. The catalyst is removed by filtration through a celite mat. The filtrate is concentrated to dryness and excess hydrochloric acid is removed by repeated co-distillation with methanol under reduced pressure to give 0.153 g. of 2'-N-glycyl-6'-N-methylfortimicin A tetrahydrochloride.

EXAMPLE 23

1,2'-di-N-benzyloxycarbonyl-6'-N-methylfortimicin B

To a stirred solution of 2.0 g. of 6'-N-methylfortimicin B, 30 ml. of water and 60 ml. of methanol, cooled in an ice bath, is added 4.44 g. of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide (23.4:1.4:0.1 v/v/v) gave 1.05 g. of product.

EXAMPLE 24

1,2'-N-di-benzyloxycarbonyl-4-N-acetyl-6'-N-methylfortimicin B

To a stirred solution of 3.22 g. of 1,2'-di-N-benzyloxycarbonyl-6'-N-methylfortimicin B in 225 ml. of methanol, cooled in an ice bath, is added 16 ml. of acetic anhydride over a 15 minute period. Stirring is continued at 0° for 2 hours and then at room temperature for 2 hours. The methanol is evaporated under reduced pressure and residual acetic anhydride and acetic acid are removed by co-distillation with benzene and methanol to leave 3.63 g. of product.

EXAMPLE 25

4-N-Acetyl-6'-N-methylfortimicin B Trihydrochloride

A solution of 1.0274 g. of 1,2'-di-N-benzyloxycarbonyl-4-N-acetyl-6'-N-methylfortimicin B in 180 ml. of 0.2 N hydrochloric acid in methanol is hydrogenolyzed over 1.25 of 5% palladium on carbon for 4 hours. The catalyst is removed by filtration through a celite mat. The filtrate is concentrated to dryness under reduced pressure and excess hydrochloric acid is removed by repeated co-distillation with methanol under reduced pressure to give 0.6595 g. of 4-N-acetylfortimicin B trihydrochloride: $[\alpha]_D^{25} + 87.2°$ (c 1.04, $CH_3OH$); IR (KBr) 1600 and 1485 $cm^{-1}$; NMR ($D_2O$) $\delta$ 1.80 ($C_6$—$CH_3$, J=6.9 Hz), 2.62 ($COCH_3$), 3.61 ($C_4$—$NCH_3$), 3.94 ($OCH_3$), 5.77 ($H_{1'}$, J=3.2 Hz); Mass spec. $M^+$. Calcd. 391.2556, measured 391.2553.

EXAMPLE 26

2-N-Acetyl-6'-N-methylfortimicin B

An aqueous solution of 0.840 g. of 4-N-acetyl-6'-N-methylfortimicin B trihydrochloride is passed through a column (1.1×19 cm) of an anion exchange resin, quaternary ammonium styrene type, e.g., Bio-Rad Laboratories' AG ® 2-X8, 50–100 mesh, hydroxyl form, sufficient to remove the chloride ion. The basic elutes are collected and diluted to 84 ml. with water. After standing at room temperature for 20 days the solution is evaporated under reduced pressure to a small volume and chromatographed on a column of a cation exchange resin, carboxylic type, e.g., Bio-Rad Laboratories' Bio-Rex 70, 100–200 mesh, ammonium form. Elution with a gradient of water to 1 N ammonium hydroxide gives fractions containing only 2'-N-acetyl-6'-N-methylfortimicin B. These fractions are concentrated to dryness under reduced pressure to give 0.390 g. of 2'-N-acetyl-6'-N-methylfortimicin B.

EXAMPLE 27

1N-Benzyloxycarbonyl-2'-N-acetyl-6',6'-di-N-methylfortimicin B

A stirred solution of 0.290 g. of 2'-N-acetyl-6',6'-N-dimethylfortimicin B in 4.5 ml. of water and 9.0 ml. of methanol, cooled to 0° in an ice bath, is treated with 0.388 g. of N-(benzyloxycarbonyloxy)succinimide. Stirring is continued at 0° for 3 hours and then at room temperature for 22 hours. The solution is concentrated under reduced pressure to an oil which is shaken with a mixture of 100 ml. of chloroform and 75 ml. of water. The chloroform layer is separated and the aqueous portion is shaken with an additional 100 ml. of chloroform. The combined chloroform solutions are washed two times with water and dried over anhydrous magnesium sulfate. Evaporation of the chloroform under reduced pressure leaves 0.480 g. of colorless solid. The solid is chromatographed on a column (2.0×43 cm) of silica gel prepared and eluted with a solvent system consisting of chloroform, methanol, ammonium hydroxide (23.4:1.4:01 v/v/v) to give 0.152 g. of product.

EXAMPLE 28

1-N-benzyloxycarbonyl-2'-N-acetyl-6',6'-di-N-methylfortimicin A

To a stirred solution of 0.150 g. of the compound of Example 27, 0.065 g. of N-benzyloxycarbonylglycine and 0.074 g. of 1-hydroxybenzotriazole monohydrate in 2.0 ml. of tetrahydrofuran is added a solution of 0.069 g. of N,N'-dicyclohexylcarbodiimide in 2.0 ml. of tetrahydrofuran. Stirring is continued at room temperature for 23 hours. The precipitated N,N'-dicyclohexylurea is removed by filtration. The filtrate is evaporated under reduced pressure to leave 0.299 g. of product. The product is chromatographed on a column of silica gel, prepared and eluted with a solvent system consisting of benzene-methanol-95% ethanol-ammonium hydroxide (23.5:1.4:2.0:0.2 v/v). Fractions containing the desired product were taken to dryness under reduced pressure leaving 0.178 g. of product.

EXAMPLE 29

2'-N-Acetyl-6',6'-N-dimethylfortimicin A Trihydrochloride

A solution of 0.178 g. of di-N-benzyloxycarbonyl-2'-N-acetyl-6',6'-di-N-methylfortimicin A in 30 ml. of 0.2 N hydrochloric acid in methanol is hydrogenolyzed for 4 hours under 3 atmospheres of hydrogen in the presence of 0.178 g. of 5% palladium on carbon. The catalyst is removed by filtration through a celite mat. The filtrate is concentrated to a small volumn and treated with activated carbon, e.g., Darco® G-60, Atlas Chemical Industries, Inc. The carbon is removed by filtration through a celite mat. The filtrate is concentrated to dryness and excess hydrochloric acid is removed by repeated co-distillation with methanol under reduced pressure to give 0.118 g. of product.

EXAMPLE 30

2'-N-(β-Aminoethyl)-6'-N-ethylfortimicin B

A stirring solution of 2.0 g. of 2'-N-glycyl-6'-N-ethylfortimicin B in 80 ml. of tetrahydrofuran is treated with 1.22 g. of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml. of water and centrifuged. The combined supernatants are taken to dryness under reduced pressure to give 1.44 g. of brown solid. The solid is chromatographed on a column (2.0×40 cm) of cation exchange resin, carboxylic type, e.g., Bio-Rad Laboratories, Bio-Rex 70, 100–200 mesh, ammonia form, and eluted with a gradient of water to 1 N ammonium hydroxide. Fractions containing the desired product are concentrated to a small volumn and lyophilized to give 0.825 g. of 2'-N-(β-aminoethyl)-6'-N-ethylfortimicin B.

EXAMPLE 31

1-N-Benzyloxycarbonyl-2'-N-[N-benzyloxycarbonyl (β-aminoethyl)]-6'-N-ethylfortimicin B A stirred solution of 0.824 g. of 2'-N-(β-aminoethyl)-6'-N-ethylfortimicin B in 12.4 ml. of water and 24.8 ml. of methanol cooled to 4° in an ice bath, is treated with 1.83 g. of N-(benzyloxycarbonyloxy)succinimide. Stirring is continued at 4° for 3 hours and then at room temperature for 22 hours. The reaction mixture is concentrated to an oil under reduced pressure and then it is shaken with a mixture of 150 ml. of chloroform and 75 ml. of water. The chloroform layer is separated and washed with 75 ml. of water. The aqueous portions are then washed in series with two 80 ml. portions of chloroform. The combined chloroform solution is dried over anhydrous magnesium sulfate and concentrated to dryness under reduced pressure to give 1.584 g. of colorless solid. The solid is chromatographed on a column (2.2×65 cm) of silica gel prepared and eluted with a solvent system consisting of benzene-methanol-95% ethanol-ammonium hydroxide (23.5:1.4:2.0:0.2 v/v/v/v) to give a 0.589 g. of product.

EXAMPLE 32

1-N-Benzyloxycarbonyl-4-N-(N-benzyloxycarbonylglycyl)-2'-N-[N-benzyloxycarbonyl-(β-aminoethyl)]-6'-N-ethylfortimicin B A stirred solution of 0.503 g. of di-N-benzyloxycarbonyl-2'-N-[N-benzyloxycarbonyl(β-aminoethyl)]-6'-N-ethylfortimicin B in 3.4 ml. of tetrahydrofuran is treated with 0.223 g. of the N-hydroxysuccinimide ester of N-benzyloxycarbonylglycine. After stirring for 20 hours at room temperature the tetrahydrofuran is evaporated under reduced pressure to leave 0.714 g. of colorless solid. The solid is chromatographed on a column (1.5×74 cm) of silica gel eluted with a solvent system consisting of benzene-methanol-95% ethanol-ammonium hydroxide (23.5:1.4:2.0)0.2 v/v/v/v) to give 0.405 g. of product.

EXAMPLE 33

2'-N-(β-Aminoethyl)-6'-N-ethylfortimicin A pentahydrochloride

A solution of 0.426 g. of 1-N-benzyloxycarbonyl-4-N-(N-benzyloxycarbonylglycyl)-2'-N-[N-benzyloxycarbonyl(β-aminoethyl)]-6'-N-ethylfortimicin B in 70 ml. of 0.2 N methanolic hydrochloric acid is hydrogenolyzed over 0.40 g. of 5% palladium on carbon for 4 hours. The catalyst, collected by filtration through a celite mat, is washed with several small portions of methanol. The filtrate is evaporated to dryness under reduced pressure. Excess hydrochloric acid is removed by repeated co-distillation with methanol under reduced pressure to give 0.268 g. of product.

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 100 mg/kg of body weight daily are administered to a mammalian patient suffering from an infection caused by susceptible organism.

We claim:

1. A 2'-N-substituted fortimicins A and B of the formula:

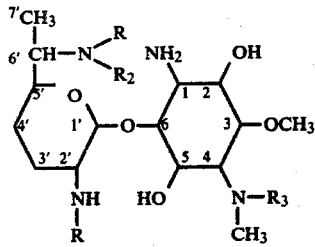

wherein: R is acyl

wherein Y is loweralkyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, or N,N-diloweralkylaminohydroxyloweralkyl; $R_1$ is loweralkyl; $R_2$ is hydrogen or loweralkyl; and $R_3$ is acyl

wherein Y is loweralkyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen; and the pharmaceutically acceptable salts thereof.

2. A compound of claim 1 wherein $R_3$ is hydrogen.

3. A compound of claim 2: 2'-N-glycyl-6'-N-methylfortimicin B or a pharmaceutically acceptable salt thereof.

4. A compound of claim 2: 2'-N-acetyl-6'-N-methylfortimicin B or a pharmaceutically acceptable salt thereof.

5. A compound of claim 2: 2'-N-(β-aminoethyl)-6'-N-methylfortimicin B or a pharmaceutically acceptable salt thereof.

6. A compound of claim 1 wherein both R and $R_3$ are an amino acid residue.

7. A compound of claim 1 wherein R is aminoloweralkyl.

8. A compound of claim 1 wherein R is an amino acid residue.

9. A pharmaceutical composition comprising a compound of claim 1 and a pharmaceutically acceptable carrier or diluent.

10. A method of treating infection comprising administering a therapeutically effective amount of a compound of claim 1 to a mammalian patient infected with one or more susceptible organisms.

* * * * *